United States Patent [19]

Johns et al.

[11] 4,314,344

[45] Feb. 2, 1982

[54] METHOD AND APPARATUS FOR GENERATING SELECTED GAS CONCENTRATIONS

[75] Inventors: Robert K. Johns, West Covina; Donald W. Deist, Glendale; Owen M. Houston, Moor Park, all of Calif.

[73] Assignee: Dasibi Environmental Corporation, Glendale, Calif.

[21] Appl. No.: 117,258

[22] Filed: Jan. 31, 1980

[51] Int. Cl.³ .................. G06F 15/46; C01B 13/12; G05D 25/02
[52] U.S. Cl. .................. 364/500; 23/232 E; 204/157.1 R; 204/176; 235/92 CA; 364/510; 364/571; 422/186.7; 422/186.30
[58] Field of Search .............. 364/118, 571, 510, 497, 364/498, 500, 496; 250/205, 573, 532, 535; 73/23; 23/232 E; 422/98; 204/157.1, 176; 235/92 CA, 92 CT, 92 CC, 92 EV

[56] References Cited

U.S. PATENT DOCUMENTS

| | | | |
|---|---|---|---|
| 3,752,748 | 8/1973 | McMillan, Jr. | 204/157.1 R |
| 3,812,330 | 5/1974 | Bowman et al. | 235/92 CC |
| 3,899,684 | 8/1975 | Tenney | 250/535 |
| 4,138,724 | 2/1979 | Kawauchi | 204/176 X |
| 4,166,784 | 9/1979 | Chapin et al. | 250/573 X |
| 4,167,665 | 9/1979 | Johns et al. | 250/205 |

*Primary Examiner*—Joseph F. Ruggiero
*Attorney, Agent, or Firm*—Lyon & Lyon

[57] ABSTRACT

A method and apparatus for generating an adjustable concentration of a selected gas within a carrier gas flow including a gas generator which is responsive to a drive signal. A gas analyzer detects the selected gas concentration within the carrier gas flow from the gas generator and provides a signal proportional to the measured concentration to a comparator. A gas concentration selector provides a second signal to the comparator, the signal being proportional to a desired concentration of the selected gas. In response to these signals, the comparator adjusts the drive signal to correct the gas generator output for the difference between the signals and to thereby substantially adjust the concentration of the selected gas within the carrier gas flow to the desired concentration. The method and apparatus automatically corrects for drift or other inaccuracies associated with the generation of the selected gas.

15 Claims, 4 Drawing Figures

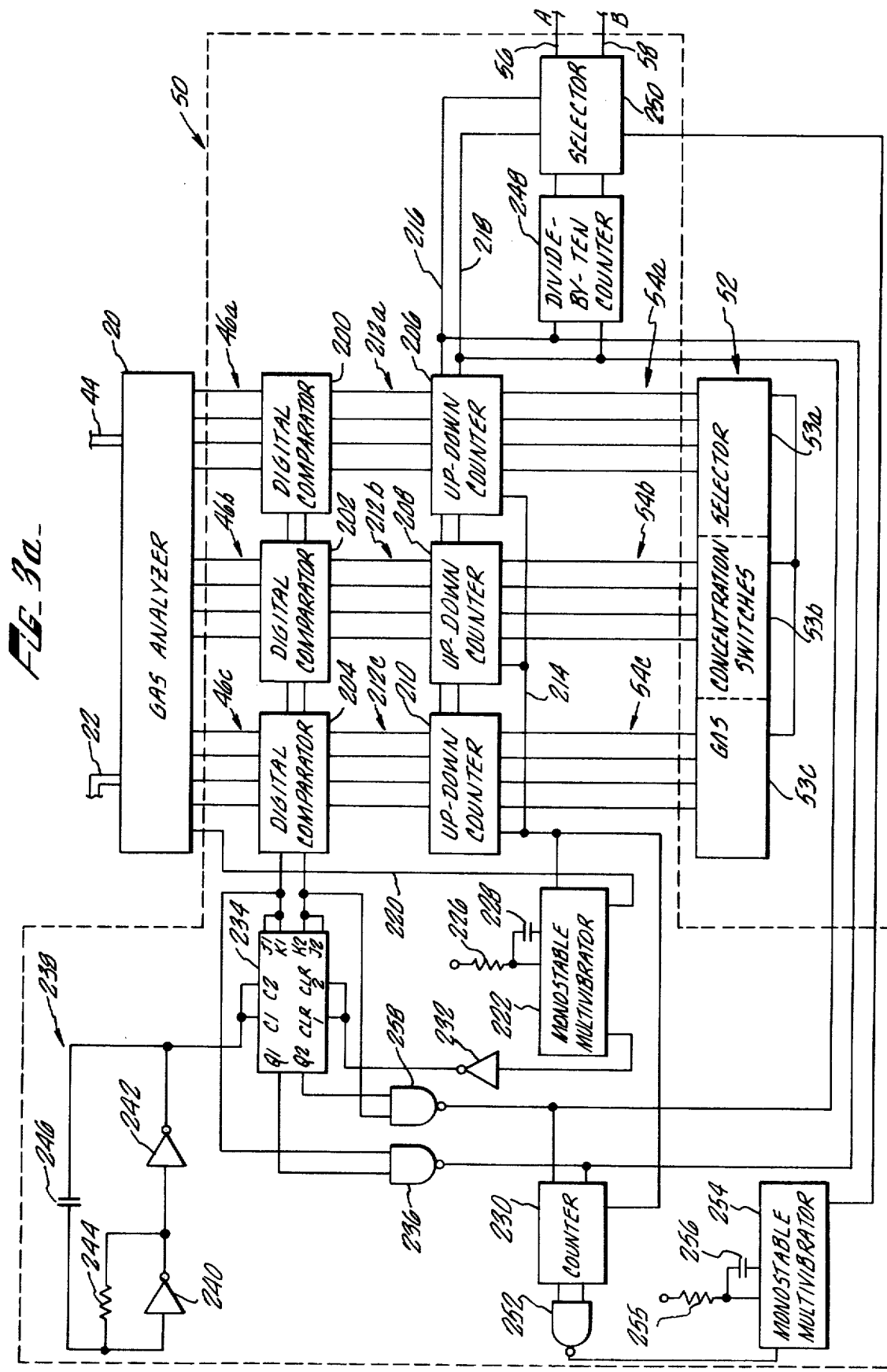

METHOD AND APPARATUS FOR GENERATING SELECTED GAS CONCENTRATIONS

FIELD OF THE INVENTION

This invention relates generally to gas calibration devices and methods and more particularly to a method and apparatus for generating predetermined selected gas concentrations within a carrier gas flow.

BACKGROUND

Various methods and devices are known for producing a predetermined concentration of a selected gas within a carrier gas flow. For example, a flow dilution technique may be used where the selected gas is stable and may be stored in a known concentration within a pressure vessel. One such gas is carbon monoxide (CO).

To perform the flow dilution technique, a first mass flow controller is used to establish a predetermined flow rate for the selected gas from a pressure vessel and a second mass flow controller similarly establishes a flow rate for a carrier gas. The carrier gas may be supplied from the atmosphere by means of a pump or from a pressure vessel depending upon the type of gas required. The flow of the selected gas is allowed to combine with the flow of the carrier gas, thereby diluting the selected gas to a concentration that is determined by several factors, including the stored concentration of the selected gas and the flow rates determined by the mass flow controllers. The accuracy of this technique depends at least in part upon the accuracy to which the known concentration of the selected gas in its pressure vessel may be determined, the purity of the carrier gas and the accuracy of the mass flow controllers.

Where the selected gas cannot be successfully compressed and stored in an accurately known concentration within a pressure vessel, as with a gas that may be reactive or unstable, a suitable gas generator may be employed to provide the selected gas within a carrier gas flow.

One such gas is ozone ($O_3$) which may be produced by exposing oxygen ($O_2$) to ultraviolet light having a wavelength of approximately 186 nm. Typically, an ozone generator using this technique may include a chamber through which a carrier gas including oxygen is passed. An ultraviolet lamp is disposed within the chamber and emits ultraviolet light in proportion to the power that is applied to the lamp. The ultraviolet light photochemically reacts with a portion of the oxygen and thereby forms ozone within the carrier gas flow. The ozone concentration produced by such an ozone generator, however, is in most instances not constant, i.e., drifts, and thus such a generator is generally not a suitable source for precise concentrations of ozone. This drift may result from, for example, fluctuations in the lamp intensity as the lamp ages, variations in the power that is applied to the lamp, inadequate circulation of the carrier gas around the lamp within the chamber, variations in the concentration of oxygen within the carrier gas flow, and temperature and pressure variations within the generator.

An ozone generating apparatus that attempts to minimize drift is disclosed in U.S. Pat. No. 3,752,748 to McMillan, Jr. The apparatus includes an ultraviolet lamp within a chamber and a detector which senses the intensity of the ultraviolet light emitted by the lamp. The power applied to the lamp is then adjusted to compensate for detected variations in this intensity. A telescoping tube mechanism is disposed around the lamp and by adjusting the length of the tube, the quantity of ultraviolet light within the chamber may be controlled to thereby vary the ozone concentration produced in the carrier gas. This apparatus remains subject to undesirable drift because, for example, the sensitivity of the detector may vary as it ages and as it is subjected to temperature variations. Also, the telescoping tube mechanism is relatively complex to manufacture and may introduce inaccuracies into the ozone concentration because of mechanical wear associated with the various components.

A second gas that may be considered exemplary of gases that cannot be readily stored is nitrogen dioxide ($NO_2$). A first technique that may be used to introduce nitrogen dioxide gas into a carrier gas flow is known as permeation, wherein liquified nitrogen dioxide is sealed within a permeable tube which may be of teflon. For the particular tube, a permeation constant may be determined which relates the temperature of the tube to the rate at which the nitrogen dioxide permeates the the tubing walls. By adjusting the temperature of the tube, the permeation rate varies and an adjustable concentration of nitrogen dioxide may be introduced into a carrier gas which is allowed to flow around the tube. Accurate temperature control of the tube is difficult, however, and the tube itself may not display the permeation characteristics upon which the accuracy of the device may depend.

A second technique that may be used to introduce nitrogen dioxide into a carrier gas flow is gas phase titration. As is well known to those skilled in the art, this technique is based on the following empirical chemical equation:

$$O_3 + NO \rightarrow NO_2 + O_2$$

With this technique, excess nitric oxide (NO) is allowed to react with a predetermined concentration of ozone provided by an ozone generator. Although the above equation predicts that one molecule of nitrogen dioxide will be produced for every molecule of ozone consumed until no ozone remains, various factors, including reaction time, influence the completeness of this reaction. Also, the ozone generator will be subject to drift as described above which will result in a corresponding drift in the $NO_2$ concentration.

SUMMARY OF THE INVENTION

The method and apparatus of the present invention provides a predetermined concentration of a selected gas in a carrier gas flow that is relatively free of drift and the inaccuracies associated with the above-described techniques. Thus the method and apparatus is suitable for use as a calibration source for various instruments which measure the concentration of the selected gas within a carrier gas, for example, apparatus for monitoring ambient air quality.

Accordingly, the present invention includes a gas generator which may employ, for example, one of the gas generation techniques previously described which introduce a selected gas into a carrier gas flow. The output gas flow from the generator is sampled by means of a gas analyzer to determine the selected gas concentration therein and the gas analyzer provides a corresponding signal to a comparator. The remaining input to the comparator is provided by a gas concentration selector and the comparator then generates an output signal that is proportional to the difference between the applied signals. The comparator output signal is applied as feedback to adjust the gas generator substantially to match the concentration of the selected gas from the gas generator to the selected concentration.

As will be recognized by one skilled in the art, the method and the apparatus of the present invention provide improved accuracy and stability generally independent of the stability of the gas generator alone by the feedback control of the gas generator. This permits the gas generator to be of a relatively simple and inexpensive design while at the same time providing good performance.

It is thus an object of this invention to provide an improved method and apparatus for generating a predetermined concentration of a selected gas within a carrier gas flow.

It is another object of this invention to provide an adjustable concentration of a selected gas within a carrier gas flow.

It is a further object of this invention to provide a selected gas at an adjustable but stable concentration within a carrier gas flow.

BRIEF DESCRIPTION OF THE DRAWINGS

The invention, including further objects and advantages thereof, may be better understood by referring to the following detailed description of alternative preferred embodiments of the invention taken in conjunction with the accompanying drawings in which:

FIGS. 3a and 3b taken together are a detailed schematic diagram of the comparator and lamp driver of FIGS. 1 and 2.

DETAILED DESCRIPTION OF THE INVENTION

Figure 1:
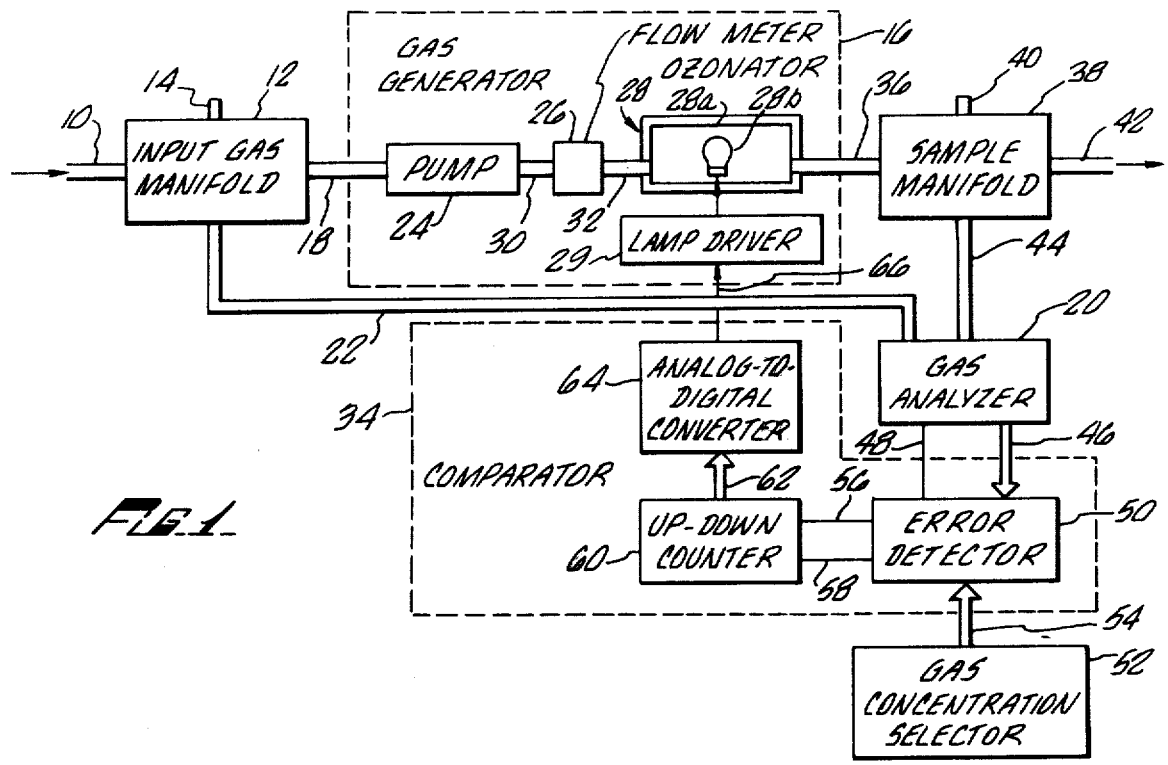
FIG. 1 is a block diagram of an apparatus for providing controlled concentrations of ozone within a carrier gas according to the present invention.

With reference now to FIG. 1, an input gas flow is applied through a conduit 10 to an input gas manifold 12. The input gas is preferably of known concentrations of specified gases which may be, for example, thirty percent oxygen and seventy percent nitrogen. The manifold 12 includes a vent 14 that is open to atmospheric pressure and two conduits 18 and 22 connect the manifold 12 to a gas generator 16 and to a gas analyzer 20 respectively. The input gas flow rate through the conduit 10 into the manifold 12 is adjusted to exceed the input flow rate requirements of the gas generator 16 and the gas analyzer 20. The excess input gas flow is vented to atmospheric pressure through the vent 14 to provide a source of input gas from the manifold 12 to the gas generator 16 and the gas analyzer 20 that remains substantially at atmospheric pressure.

The gas generator 16 includes a pump 24, a flow meter 26 and an ozonator 28 serially connected by two conduits 30 and 32. The pump 24 draws input gas from the manifold 12 through the conduit 18 and provides that input gas flow at a flow rate determined by the flow meter 26 to the ozonator 28. The ozonator 28 is of conventional design and may include a chamber 28a within which is disposed an ultraviolet lamp 28b. The input gas flow enters the chamber 28a through the conduit 32 and surrounds the ultraviolet lamp. The ultraviolet lamp 28b is powered by a lamp driver 29 which is responsive to an analog drive signal from comparator 34 as will be described subsequently. The ultraviolet lamp 28b illuminates in response to this drive signal and generates ultraviolet light which photochemically reacts with a portion of the oxygen within the input gas flow to produce ozone. The concentration of ozone within the gas flow is proportional to, among other factors, the ultraviolet light intensity and the flow rate of the gas through the chamber 28a. Since the flow rate of the input gas is maintained at a substantially constant value by the flow meter 26, it will be seen that the ozone concentration within the gas flow is thus substantially proportional to the ultraviolet light intensity which in turn is proportional to the analog drive signal. It will also be apparent that the production of ozone within the ozonator alters the original concentration of oxygen within the input gas flow. Thus, the resulting gas flow from the ozonator 28 may be properly considered to be a resulting concentration of ozone within a carrier gas flow.

To improve the stability of the ozonator 28, the chamber 28a may be thermally isolated from the environment and further include a heating element and a temperature sensor which cooperate to maintain a substantially constant temperature within the chamber 28a of the ozonator 28. The circuitry required for this temperature sensing and heating element will be more fully described with reference to FIG. 3b.

The gas from the chamber 28a is applied through a conduit 36 to a sample manifold 38. The sample manifold 38 is similar in construction to the manifold 12 and includes a vent 40 to atmospheric pressure. A conduit 42 is connected to the sample manifold 38 and may typically be connected to an instrument such as an ambient air quality monitoring apparatus which may include a pump that will draw the ozone and carrier gas flow from the sample manifold 38. A second conduit 44 is connected from the sample manifold 38 to the gas analyzer 20.

The flow rate established by the flow meter 26 and conducted by means of the conduit 32, the ozonator 28 and the conduit 36 to the sample manifold 38 is greater than the requirements of an instrument that may be connected to the conduit 42 and the requirements of the gas analyzer 20. Thus, similarly to the vent 14 of the input gas manifold 12, the vent 40 vents the excess gas flow to atmosphere and maintains the sample manifold 38 substantially at atmospheric pressure. In this way, the manifolds 12 and 38 provide a source of gas at atmospheric pressure for the gas analyzer 20 and the instrument that may be connected through the conduit 42 to the manifold 38.

The gas analyzer 20 is preferably a photometer having at least a two percent absolute accuracy such as that disclosed in U.S. Pat. No. 3,812,330 to Bowman et al. which is incorporated herein by reference. The gas analyzer 20 alternately samples the input gas at atmospheric pressure from the manifold 12 through the conduit 22 and the gases at atmospheric pressure from the sample manifold 38 through the conduit 44. The gas analyzer 20 then determines the concentration of ozone within the carrier gas flow contained in the sample manifold 38 and generates a plurality of digital signals on lines 46 that are proportional to the measured ozone concentration. The gas analyzer 20 also generates a strobe signal on a line 48 which indicates that the gas analyzer 20 has completed the measurement process and that the digital signals on the lines 46 have been updated and substantially represent the present ozone concentration within the carrier gas flow. The gas analyzer 20 repeats this sample and measurement process periodically, generating updated signals on the lines 46 and a strobe signal on the line 48 with each complete cycle.

The digital signals applied on lines 46 may be generated within the gas analyzer 20 to provide a suitable digital display of ozone concentration. For example, the digital signals may be those that are used within the gas analyzer 20 to drive a decoder, driver and digital display as is well known in the art and which is illustrated with reference to FIG. 1 of the Bowman et al. patent. Similarly, the strobe signal applied on line 48 may be developed within the gas analyzer 20 to latch the data signals into a memory and a buffer and to thereby update the digital display of the gas analyzer 20.

The lines 46 and 48 connect the digital signals and the strobe signal previously described to an error detector 50, part of the comparator 34. The error detector 50 is also responsive to a plurality of digital signals generated by a gas concentration selector 52, which are applied to the error detector 50 via lines 54. The gas concentration selector 52, as will be explained with reference to FIG. 3a, may include a plurality of switches that are adjustable to a desired ozone concentration and which then provide the digital signals in proportion to the desired concentration. The selector 52 may be replaced by other suitable external sources such as a computer which may be part of an automated testing apparatus.

When the strobe signal appearing on line 48 indicates that the digital signals from the gas analyzer 20 have been updated, the error detector 50 compares the digital signals applied by the lines 46 with the digital signals applied by the lines 54 and provides a signal pulse train that is proportional to the difference between the concentrations represented by these two sets of digital signals. If, for example, the measured concentration of ozone as indicated by the digital signals on the lines 46 is greater than the desired concentration of ozone as represented by the digital signals appearing on the lines 54, the signal pulse train will be applied to a first output line 56.

In a similar fashion, if the ozone concentration measured by the gas analyzer 20 is less than the desired ozone concentration selected by means of the gas concentration selector 52, the comparator 50 generates a signal pulse train proportional to the difference on a second output line 58. As is to be appreciated, as the difference between the measured and desired ozone concentration decreases, the number of pulses or length of the signal pulse train decreases proportionally until comparatively few or no pulses are generated by the error detector 50 with each strobe signal.

The lines 56 and 58 are connected to an up-down counter 60 such that the counter 60 is counted up by the signal pulse train if the measured ozone concentration is greater than the desired concentration and is counted down if the measured ozone concentration is less than the desired concentration. The up-down counter 60 generates a plurality of digital outputs that are connected by means of lines 62 to a digital-to-analog converter (DAC) 64. The digital signals developed by the counter 60 are converted by the DAC 64 to an analog drive signal which increases in magnitude as the count decreases or, conversely, decreases in magnitude as the count increases. Thus the magnitude of the analog drive signal increases when the measured ozone concentration is less than the desired concentration and vice versa. The analog signal is connected through the line 66 to the lamp driver 29. This analog drive signal controls the intensity of the ultraviolet lamp contained within the ozonator 28 and thus controls the concentration of ozone within the carrier gas flow so as to decrease the difference between the measured ozone concentration produced by the gas generator 16 and the desired ozone concentration.

This correction of the ozone concentration produced by the gas generator 16 will be repeated with each periodic strobe signal from the gas analyzer 20. As this correction process continues, the difference will decrease and the length of the signal pulse train will correspondingly decrease until the gas generator 16 is adjusted a comparatively insignificant amount or not at all with each strobe signal from the gas analyzer 20. If the ozone concentration generated by the gas generator 16 should vary or drift from the desired concentration, the error detector 50 will adjust the counter 60 and thus the analog drive signal to thereby correct for the variation in the manner just described.

Thus the apparatus of FIG. 1 provides a selected concentration of ozone within a carrier gas flow which is extremely accurate and which is also free from drift and other inaccuracies which would be normally associated with a gas generator 16.

Figure 2:
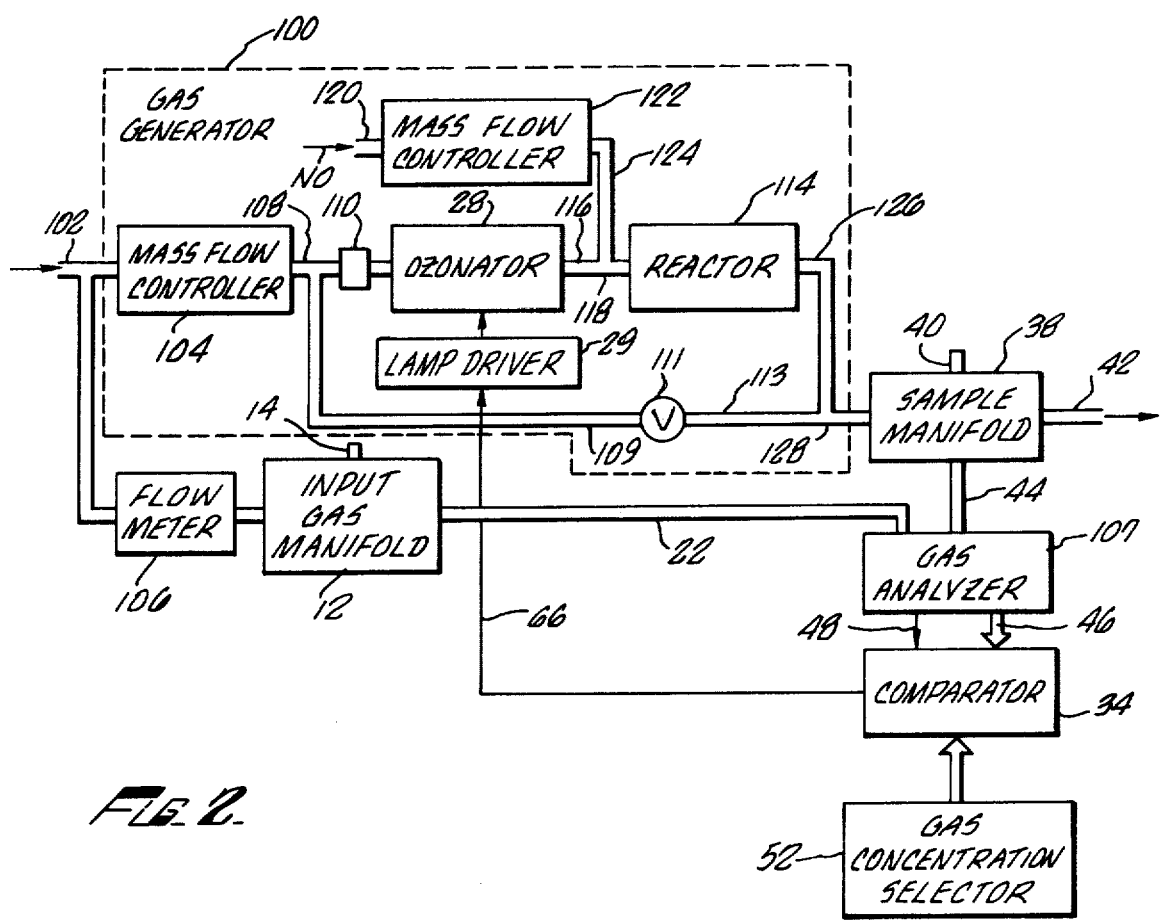
FIG. 2 is a block diagram of an apparatus employing the invention for generating stable concentrations of nitrogen dioxide within a carrier gas flow.

As will be recognized by those skilled in the art, the apparatus of FIG. 1 may be adapted to provide a selected concentration of nitrogen dioxide in a carrier gas flow by replacing the gas generator 16 of FIG. 1 with a nitrogen dioxide gas generator 100 of FIG. 2. In FIG. 2, those elements which are substantially similar to the elements of FIG. 1 bear identical reference numerals.

In FIG. 2, input gas is applied through a conduit 102 to a mass flow controller 104 of the gas generator 100. The conduit 102 also conducts the input gas to a flow meter 106 which is in turn connected to the input gas manifold 12. The manifold 12 includes the vent 14 and is connected by the conduit 22 to a gas analyzer 107.

Returning to the gas generator 100, the mass flow controller 104 is adjusted to provide a predetermined flow rate through the conduit 108. The conduit 108 is connected through a restrictor 110 to the ozonator 28 and through a conduit 109, a flow metering valve 111 and a conduit 113 to a tee 128. The tee 128 is also connected through a conduit 126 to the output of a reactor 114 and to the sample manifold 38. The flow metering valve 111 is adjusted so that approximately ten percent of the total flow determined by the mass flow controller 104 is forced through the restrictor 110 to the ozonator 28. The remaining approximately ninety percent of the flow is bypassed through the metering valve 111 to the output of the reactor 114. As previously described, the ozonator 28 generates ozone in response to the analog drive signal from the comparator 34, the concentration of ozone being proportional to the magnitude of the signal. The ozone from the ozonator 28 is conducted through a conduit 116 to a tee 118.

A supply of nitric oxide (NO) is provided from a suitable source through a conduit 120 to a mass flow controller 122. The mass flow controller 122 is adjusted to provide a predetermined flow rate through a conduit 124 to the tee 118. The third outlet of the tee 118 is connected to the input of the reactor 114.

As will be apparent from the previous discussion concerning gas phase titration, the gas generator 100 produces NO₂ by allowing NO to react with O₃. To ensure that this reaction is complete, the mass flow controller 122 is adjusted so that the concentration of NO substantially exceeds the amount of ozone which will be introduced from the ozonator 112 through the conduit 116 and tee 118 to the reactor 114. The reactor 114 may be a vessel of suitable volume such that the gas phase titration reaction is allowed to be substantially completed, that is, until approximately 99% of the ozone supplied by the ozonator 112 has been converted to NO₂. The resulting NO₂ from the reactor 114 is provided through the conduit 126 to the tee 128 where the gas flow from the mass flow controller 104 is combined with the gas flow from the reactor 126 and is in turn supplied to the sample manifold 38.

Thus, the gas generator 100 produces a concentration of NO₂ in a carrier gas flow that may be controlled by adjusting the analog signal applied to the ozonator 112. As will be apparent to those skilled in the art, an adjustment may also be made by adjusting the mass flow controller 122 and thus the quantity of NO that is allowed to react with ozone. It is preferred, however, to provide excess NO through the mass flow controller 122 and to then control the ozone concentration by means of the ozonator 28 to vary the concentration of the resulting NO₂.

The sample manifold 38 includes the vent 40 and the conduit 42 through which an instrument under calibration, for example, may be connected. The sample manifold is also connected through the conduit 44 to the gas analyzer 107. The gas analyzer 107 is preferably a photometer which determines the concentration of NO₂ within the carrier gas flow through the sample manifold 38 and may be substantially similar in operation to the gas analyzer 20 of FIG. 1. A plurality of digital signals proportional to this concentration are provided by the gas analyzer 107 through the lines 46 to the comparator 34.

As has been described previously with reference to FIG. 1, the apparatus of FIG. 2 includes the comparator 34, and the gas concentration selector 52 which may be considered to be substantially similar to those described for FIG. 1.

The operation of the apparatus of FIG. 2 is similar to the apparatus of FIG. 1. In FIG. 2, a NO₂ concentration is produced in a carrier gas flow by means of the gas generator 100 in response to the analog drive signal applied through the line 66 to the ozonator 28. The gas analyzer 107 determines the concentration of NO₂ contained in the carrier gas flow and, with each strobe signal from the analyzer 107, the comparator 34 compares this measured concentration with a desired concentration set by the gas concentration selector 52. The comparator 34 then adjusts the analog drive signal by an amount that is proportional to the difference between the measured concentration and the desired concentration so as to correct the NO₂ concentration generated by the generator 100. This difference decreases until, with each strobe signal from the gas analyzer 107, the analog output drive signal from the comparator 34 is adjusted a comparatively insignificant amount or not at all. The operation of the comparator 34 will be described in greater detail with reference to FIG. 3.

Thus, the apparatus of FIG. 2, in a manner similar to that of the apparatus of FIG. 1, generates an accurate, selectable concentration of NO₂ within a carrier gas flow. This selectable concentration is stable over relatively long periods of time and is maintained more accurately than would be otherwise possible with the gas generator 100 alone. It should be noted that this improved concentration accuracy and stability with respect to the NO₂ gas generator 100 will result whether the gas generator 100 is controlled through the mass flow controller 122 or by varying the lamp intensity within the ozonator 28.

It will be further noted and understood by those skilled in the art that the gas generators 16 and 100 of FIGS. 1 and 2 respectively may be replaced by other suitable generator means, such as permeation or flow dilution techniques. For example, the gas generator 100 of FIG. 2 may be replaced by a permeation device for generating NO₂ as was described above. The analog drive signal from the comparator 34, instead of controlling the ozonator 28 or the mass flow controller 122 of FIGS. 1 and 2, would instead control the temperature of the permeation tube or more preferably the carrier gas flow through the permeation device and thus the concentration of NO₂. Such a suitable gas generator means controlled in this way provides a selected gas concentration in a carrier gas flow that is determined primarily by the accuracy and stability of a gas analyzer (corresponding to 20 or 107 of FIGS. 1 or 2 respectively) rather than the accuracy and stability of the particular gas generator means employed. Thus the method and apparatus of the present invention represent a substantial improvement over existing gas generation and instrument calibration techniques.

Figure 3B:
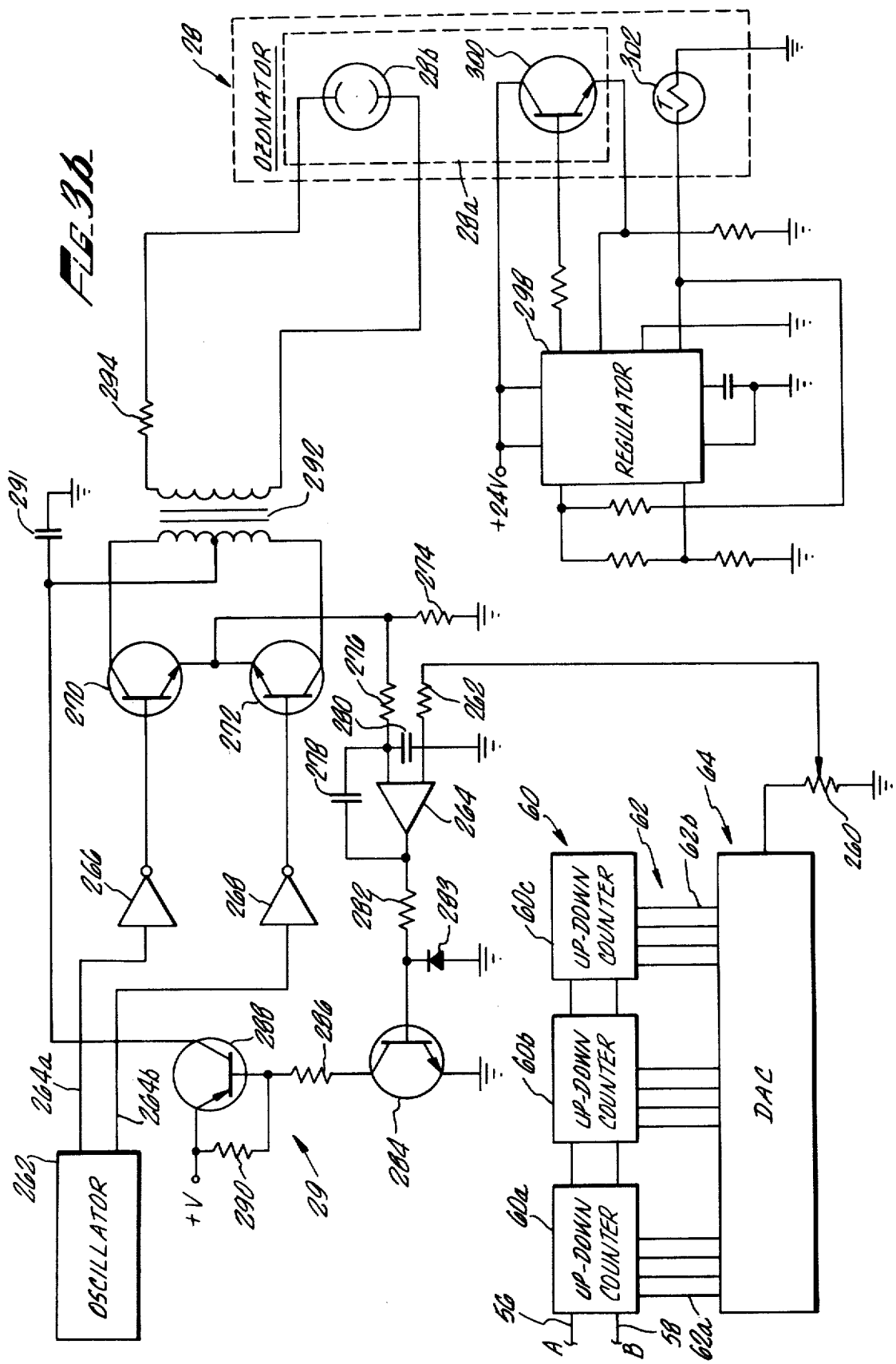

With reference now to FIGS. 3a and 3b which are joined at the letters A and B, the gas analyzer 20 generates three sets of binary coded decimal (BCD) signals which are conducted by means of three sets of lines 46a-c to three respective digital comparators, 200, 202 and 204 that are typically a type 7485. In the preferred embodiment of FIG. 3a, the BCD signals carried by the lines 46a-c may represent the measured ozone concentration within the carrier gas flow in thousandths, hundredths and tenths of a part per million, respectively. Thus, the three sets of BCD signals when taken together provide a digital representation of measured ozone concentration within the carrier gas flow to three decimal places when the ozone concentration is less than 1 part per million.

The gas concentration selector switch 52 may include three switches 53a, 53b, and 53c which generate three sets of BCD signals on the lines 54a-c. The BCD signals on the lines 54a may be adjusted by the switch 53a to represent a desired ozone concentration within the carrier gas stream in thousandths of a part per million. Similarly, the BCD signals on the lines 54b and 54c may be adjusted by means of the switches 53b and 53c to a desired ozone concentrations in hundredths of a part per million and tenths of a part per million respectively. In this way, the gas concentration selector 52 may be adjusted to provide three BCD signals sets which represent a desired ozone concentration between zero and 0.999 parts per million.

The BCD signals from the switches 53a-c are applied through the lines 54a-c to three up-down counters 206, 208 and 210. Each of the counters 206-210 which typically is a type 74192 is a decade or divide-by-ten BCD counter and provides a set of digital signals in BCD format on the lines 212a, 212b and 212c to the respective comparators 200, 202, and 204. A pre-load latch signal is applied to the counters 206-210 through a line 214, as will be described subsequently. The pre-load latch signal causes the counters 206-210 to be set or preloaded to the levels of the BCD signals appearing on the lines 54a–c, thereby causing the BCD output signals on the lines 212a–c to correspond to the respective BCD input signals appearing on the lines 54a–c.

The counter 206 is made to increase or increment its count by signals appearing on a line 216 and is caused to decrease or decrement its count by signals appearing on a line 218. As will be understood by those skilled in the art, the counter 206 provides either a borrow or a carrying signal to the counter 208 which in turn causes the counter 208 to either decrement or increment its BCD output. In turn, the counter 208 provides a borrow or a carry signal to the counter 210 causing the counter 210 to decrement or increment its BCD output. It will thus be seen that the counters 206–210 form a three decade BCD counter which may be set or preloaded to the BCD signals generated by the switches 53a–c representing a desired ozone concentration in parts per million and which may then be incremented or decremented from the preloaded count.

The gas analyzer 20 also provides a strobe signal on a line 220 to a monostable multivibrator 222. The period of the monostable multivibrator 222 is controlled in a conventional manner through a resistor-capacitor combination 226 and 228. A first output from the multivibrator 222 is connected to the line 214 to provide the preload or set signal to the counters 206–210 and is also applied to a counter 230. A second and complementary signal from the multivibrator 220 is inverted by means of an inverter 232 and is applied to the clear inputs of a dual J-K flip-flop 234 which may be a type 74107. The gas analyzer 20 generates the strobe signal when the measured ozone concentration represented in BCD format on the lines 46a–c is updated, thereby triggering the multivrator 222 and causing the desired ozone concentration selected by the switches 53a–c to be set or preloaded into the counters 206–210. The monostable multivibrator 222 also clears the flip-flop 234 through the inverter 232 and sets the counter 230 to a predetermined count which may be in an exemplary embodiment a count of five. The operation and function of the counter 230 and the flip-flop 234 will be subsequently described.

Once the gas analyzer 20 has produced the strobe signal on the line 220, the comparators 200, 202 and 204 compare the BCD signals from the gas analyzer 20 representing measured ozone concentration with the BCD signals from the counters 206, 208 and 210 which represent the desired ozone concentration as selected by the switches 53a–c and as latched into the counters 206, 208 and 210. If the magnitude of the BCD signals appearing on the lines 46 is greater than the magnitude of the BCD signals appearing on the lines 212, then the comparators 200, 202 and 204 together provide a first output signal to the J1 and K1 inputs of the flip-flop 234 and to one input of a two input NAND gate 236. This would occur, for example, if the BCD signals were to indicate that the measured ozone concentration was 0.750 parts per million and the desired ozone concentration were 0.690 parts per million.

An oscillator 238 formed from two invertors 240 and 242, a resistor 244 and a capacitor 246 connected in conventional fashion, applies a pulse train at, for example, approximately 10 KHz to the clock inputs C1 and C2 of the flip-flop 234. Once the flip-flop 234 has been cleared by the signal from the multivibrator 222 through the inverter 232 and the signal from the comparator 204 is applied to the J1-K1 inputs of the flip-flop 234, one-half of the flip-flop 234 will operate in the toggle mode and provide a series of pulses at the Q1 output having a frequency that is one-half the frequency of the oscillator 238. The signal from the Q1 output of the flip-flop 234 is applied to the gate 236 which is controlled by the signal from the comparator 204 to allow the pulses from Q1 of the flip-flop 234 to appear in an inverted state at the output of the gate 236. These pulses are in turn applied to the counter 230, to a divide-by-ten counter 248, to line 216 causing the counter 206 to increment or count up, and to a selector 250.

The counter 206 and in turn the counters 208 and 210 will continue to increment until the BCD signals appearing at the outputs thereof on the lines 212a–c are equal to the BCD signals from the gas analyzer 20. When the BCD signals applied on both sides of the comparators 200, 202 and 204 are thus equal, the comparators 200, 202 and 204 remove the signal that is applied to the J1-K1 input of the flip-flop 234 and to the gate 236. With the removal of this signal, the flip-flop 234 ceases to toggle and the gate 236 is disabled, removing the pulses from the output of the gate 236.

It will be seen that the number of pulses produced by the gate 236 in the embodiment of FIG. 3a is proportional to the difference between the measured ozone concentration and the desired ozone concentration. Assuming that the difference is as described above, that is, that the actual ozone concentration is 0.750 parts per million and that the desired ozone concentration is 0.690 parts per million, then the circuitry will operate as described to produce sixty pulses at the output of the gate 236 so as to increase the BCD outputs of the counters 206–210 from 690 to 750.

The counter 230, gate 252, multivibrator 254, counter 248 and selector 250 cooperate to provide a predetermined number of pulses either on the line 56 or the line 58 in response to the pulses generated by the gate 236 or by a NAND gate 258. With respect now to the counter 230 of FIG. 3a, which may be a divide-by-ten up-down center such as as a type 74192, a signal from the multivibrator 222 sets the counter 230 to a count of five as previously described. The carry and borrow outputs from the counter 230 are applied through a NAND gate 252 to a monostable multivibrator 254 which is in turn connected to the selector 250. The output pulses from the gate 236 may be connected to the counter 230 so as to increment the counter 230 and thus once the gate 236 produces five pulses, the counter 230 will generate a carry signal in anticipation of the next pulse from the gate 236 which will be applied through the gate 252 to trigger the multivibrator 254. The period of the monostable multivibrator 254 is determined in a well-known fashion by means of a resistor 255 and a capacitor 256 to be preferably longer than the time period required to increment or decrement the counters 206–210 through the maximum difference that may exist between the measured and actual ozone concentration which would be, for the exemplary embodiment of FIG. 3a, 999 pulses from either Q1 or Q2 of the flip-flop 234.

The signal from the gate 236 is also applied to the divide-by-ten up-down counter 248 which is typically a type 74192 and to the selector 250 which may be a type 74157. The counter 248 is incremented by the pulses from the gate 236 and is decremented by the pulses from the gate 258 as will be subsequently described. Thus the counter 248 is continuously responsive to the signals from the gates 236 and 258 and will provide a carry signal to the selector 250 when the gate 236 increments the counter 248 from nine to zero and will similarly provide a borrow pulse to the selector 250 when the gate 258 decrements the counter 248 from the zero to nine.

The output of the selector 250 is controlled by the signal from the multivibrator 254. Before the multivibrator 254 is triggered, the selector 250 applies the carry and borrow signals from the counter 248 to the lines 56 and 58 respectively. Once the multivibrator 254 is triggered by the counter 230 and the gate 252, the selector 250 then applies the pulses from the output of the gate 236 to the line 56 and applies the pulses from the gate 258 to the line 58. Thus, assuming that the gate 236 has begun to generate pulses as has been previously described, the selector will connect the carry output from the counter 248 to the line 56. If during this time the counter 248 should be incremented from nine to zero by the pulses from the gate 236, the carry signal generated by the counter 248 will be applied to the line 56. Once five pulses from the gate 236 have been counted by the counter 230, the multivibrator 254 is triggered prior to the sixth pulse and the selector then connects the output of the gate 236 directly to the line 56.

In this manner, the selector 250 will continuously connect the carry output from the counter 248 to the line 56 if the gate 236 generates five or fewer pulses with each strobe signal from the gas analyzer 20. When operating in this fashion, the counter 248 will divide the number of pulses from the gate 236 by ten. However, should the gate 236 generate more than five pulses, the pulses from the gate 236 will be applied by the selector 250 directly to the line 56. As will be apparent, if the measured ozone concentration applied in BCD format to the digital comparators 200-204 is within five thousandths of a part per million of the desired ozone concentration, the gate 236 will generate five or fewer pulses and thus only one pulse will appear on the line 56 for each ten pulses generated by the gate 236 and the adjustment of the ozonator 28 (FIG. 3b) through the counter 60, the DAC 64 and the lamp driver 29 will be decreased by a factor of ten. However, if the measured ozone concentration exceeds the desired ozone concentration by more than five thousandths of a part per million, then the selector 250 will first connect any carry output from the counter 248 to the line 56 for the first five pulses from the gate 236 and will then apply the pulses from the gate 236 directly to the line 56. In this way, the drive signal to the ozonator 28 will be more quickly adjusted to the desired ozone concentration. A more detailed description of the counter 60 and the lamp driver 29 will be made with reference to FIG. 3b.

Although the circuitry of FIG. 3a has been described with reference to an example wherein the magnitude of the measured ozone concentration was greater than the desired ozone concentration, the embodiment of the present invention disclosed herein functions in a similar manner to provide a signal train on the line 58 when the magnitude of the desired ozone concentration is greater than the magnitude of the measured ozone concentration.

For example, assuming that the desired ozone concentration is again 0.690 parts per million, the selector switches 53a-c may be adjusted such that the BCD signals appearing on the lines 54c are equivalent to a decimal digit six, and the BCD signals appearing on the lines 54b are equivalent to a decimal digit nine, and the lines 54a represent a decimal digit zero. Once the gas analyzer 20 has completed its measurement process, a strobe signal is applied on the line 220 and causes the multivibrator 222 to pre-load the desired ozone concentration into the up-down counters 206, 208 and 210. The multivibrator 222 will, of course, also clear the flip-flop 234 and set the counter 230 to a count of five. Assuming for the purpose of this example that the BCD signals from the gas analyzer 20 on the lines 46a-c indicate that the measured ozone concentration is 0.650 parts per million, the comparators 200-204 will apply a signal to the J2 and K2 inputs of the flip-flop 234 and to the gate 258. The flip-flop 234 will then toggle as previously described and apply a series of pulses at one-half the frequency of the oscillator 238 to the gate 258.

With the signal from the comparator 204 applied to the gate 258, the pulses from the Q2 output of the flip-flop 234 are inverted by the gate 258 and applied to the counter 230, to the line 218, to the counter 248 and to the selector 250. These pulses appearing on the line 218 cause the counters 206, 208 and 210 to be decremented or counted down. When the counter 206 has received forty pulses from the gate 258, the BCD outputs from the counters 206-210 will be equivalent to the decimal number 650 and thus equal to the BCD signals applied to the comparators 200-204 from the gas analyzer 20. The comparators 200-204 will then remove the signal from the J2-K2 inputs of flip-flop 234 and from the gate 258, terminating the pulses appearing at the output of the gate 258. Thus the counters 206-210 are operated to adjust the respective output BCD signals on the line 212a-c so as to equal the BCD signals generated by the gas analyzer 20.

In a manner similar to that previously described, the counter 230, gate 252, multivibrator 254, counter 248 and the selector 250 provides a series of pulses on the line 58 to the counter 60a (FIG. 3b) which are related in number to the difference between the measured ozone concentration and the desired ozone concentration. Once the counter 230 is preloaded to five, the pulses from the gate 258 are connected to decrement or count down the counter 230 (FIG. 3a). Before the multivibrator 254 is triggered, the pulses from the gate 258 decrement the counter 248 and the borrow output thereof is applied through the selector 250 on line 58 to the counter 60a. However, once the gate 258 provides more than five pulses to the counter 230, the multivibrator 254 is triggered and the selector 250 connects the line 58 to the gate 258.

The summarize briefly the operation of the circuitry of FIG. 3a, the comparators 200, 202 and 204 compare the measured ozone concentration in BCD format with a desired ozone concentration also in BCD format from the counters 206-210. The comparators 200-204 then control the flip-flop 234 and the gates 236 or 258 to generate a pulse train that increments or decrements the counters 206-210 to correct for a difference between the BCD signals representing the measured and desired ozone concentrations. If the number of pulses from either gate 236 or 258 is less than or equal to a predetermined number, then the pulses are applied through the counter 248 that provides a pulse to the line 56 or 58 for every ten input pulses from either gate 236 or gate 258 respectively. If the number of pulses from the gates 236 or 258 exceeds this predetermined number, the outputs from the gate 236 or 258 are connected by the selector to the lines 56 or 58. This circuitry thus scales the pulses applied to the counter 60 (FIG. 3b) by a factor of ten when the difference between the measured and desired ozone concentration is within a predetermined narrow range which in the embodiment of FIG. 3a may be plus or minus five parts per million. Outside of this narrow range, the sixth and following pulses from the gates 236 and 258 are applied directly to the counter 60 to more quickly adjust the measured ozone concentration toward the desired concentration. It is seen that the number of pulses appearing on the lines 56 or 58 is related to the difference between the BCD signals from the gas analyzer 20 and the BCD signals from the switches 52 and that these pulses will appear on the line 56 when the measured ozone concentration is greater than the desired ozone concentration. Further, the pulses on the line 58 will appear when the desired ozone concentration selected by the switches 52 is greater than the ozone concentration measured by the gas analyzer 20.

With reference now to FIG. 3b, the lines 56 and 58 are connected to the counter 60a which is one of three up-down binary counters 60a-c which comprise the counter 60 of FIG. 1. The counters 60a-c may be of a type 74193. The pulses appearing on the line 56 increment or count up the counter 60a which in turn counts up the counters 60b and 60c (FIG. 3b). Similarly, the pulses appearing on the line 58 decrement or count down the counter 60a and in turn the counters 60b and 60c. The digital outputs from the counters 60a-60c are connected through the lines 62 to the DAC 64. As will be understood by those skilled in the art, the least significant digital bit will appear on the line 62a from the counter 60a and the most significant bit will appear on the line 62b from the counter 60c.

The DAC converts the digital signals applied through the lines 62 into an analog signal which is proportional to the binary number appearing on the lines 62. The magnitude of the analog signal increases as the binary number decreases and, conversely, decreases as the binary number increases. A suitable DAC may be, for example, a DAC 80 CBI-V manufactured by Burr-Brown. In a preferred embodiment, the analog voltage output from the DAC 64 is in a range from zero to five volts. This analog output is applied to a potentiometer 260 and is adjusted thereby to produce a corresponding ozone concentration within the ozonator 28 of approximately zero parts per million to approximately 0.999 parts per million respectively. The signal from the potentiometer 260 is connected through a resistor 262 to an operational amplifier 264 which is part of the lamp driver 29.

With respect now to the lamp driver 29 of FIG. 3b, an oscillator 262 provides complementary outputs 264a and 264b at a nominal frequency of approximately 10 KHz which are applied through two buffering inverters 266 and 268 to the bases of two transistors 270 and 272 respectively. The emitters of the transistors 270 and 272 are connected together and are in turn connected through a resistor 274 to ground and through a second resistor 276 to the inverting input of the operational amplifier 264. A capacitor 278 provides negative feedback from the output of the amplifier 264 to the inverting input and a second capacitor 280 is connected between the inverting input and ground.

The output of the amplifier 264 is applied through a resistor 282 to the base of an NPN transistor 284. The cathode of a protection diode 283 is connected to the base of the transistor 284 and the anode of the diode 283 is connected to ground. The emitter of the transistor 284 is connected to ground and the collector is connected through a resistor 286 to a series pass transistor 288 which includes a bias resistor 290 in a conventional fashion between the emitter and base thereof. A positive voltage is applied to the emitter of the transistor 288 and the drive signal from the transistor 284 controls the current that flows from the collector of the transistor 288 through the center tap of the primary winding of a transformer 292. A first end tap of the transformer 292 primary winding is connected to the collector of the transistor 270 and a second end tap of the primary winding is connected to the collector of the transistor 272.

The secondary winding of the transformer 292 is connected in series with a limiting resistor 294 and the ultraviolet lamp 28b. The lamp 28b is disposed within the ozonator 28 and may be a model number L937-069 manufactured by Hamamatsu. The lamp preferably emits ultraviolet radiation at a wavelength of substantially 186 nm.

In the operation of the lamp driver 29, the oscillator 262 drives the transistors 270 and 272 so as to alternately conduct current supplied by the transistor 288 through the primary winding of the transformer 292. This current in turn develops a voltage across the resistor 274 which is proportional to the current flowing through the primary of the transformer 292. This proportional voltage is applied through the resistor 276 to the inverting input of the amplifier 264. The amplifier 264 compares this feedback voltage with the analog drive signal from the potentiometer 260 as applied through the resistor 262 and in turn develops a drive signal which is amplified by the transistor 284 to control the current flowing through the transistor 288 and thus the current flowing through the primary of the transformer 292. The secondary of the transformer 292 produces a stepped-up output which illuminates the lamp 28b with an intensity that is proportional to the current flowing through the primary. Thus, the analog drive signal from the potentiometer 260 through a feedback circuit controlled by the amplifier 264 controls the illumination intensity of the lamp 28b and thereby controls the concentration of ozone generated within the ozonator 28.

In summary, then, the error detector 50 of FIG. 3a provides a series of pulses on the line 56 if the measured ozone concentration is greater than the desired ozone concentration as selected by the selector switches 52. These pulses cause the counters 60a-60c to count up and to thus decrease the analog output from the DAC 64 as applied through the potentiometer 260. This decreased analog drive signal causes the lamp driver 29 of FIG. 3b to decrease the drive to the lamp 28b and to thus decrease the concentration of ozone produced within the input gas flow by the ozonator 28. As the measured ozone concentration nears the desired concentration, the number of pulses appearing on the line 56 from the error detector 50 decreases and thus the drive to the lamp 28b is adjusted by a gradually decreasing amount. Once the intensity of the lamp 28b has been adjusted so that the difference between the desired and measured concentration is within a predetermined narrow range, the output of comparator is scaled to decrease the rate of change of the lamp 28b output. The comparator will then operate to gradually approach the desired ozone concentration.

Similarly, if the initial ozone concentration within the carrier gas flow is less than the desired concentration, then a series of pulses will be provided on the line 58 by the error detector 50 to the counter 60a and in turn to the counters 60b and 60c. This pulse train will cause the counter 60a-60c to be counted down or decremented thus increasing the analog output from the DAC 64 and in turn the analog drive signal from the potentiometer 260 as applied to the amplifier 264 of the lamp driver 29. This increasing analog drive signal will increase the drive provided to the lamp 28b, thus increasing the ozone concentration within the carrier gas flow. Once the difference between the measured concentration and the desired concentration of ozone is within a predetermined narrow range, the error detector 50 will then operate to gradually adjust the measured ozone concentration toward the desired ozone concentration.

To further stabilize the drift that may be associated with the ozonator 28 due to temperature variations, a precision voltage reference regulator 298 is connected in a conventional manner to a transistor 300. The transistor 300 may be located within the ozonator chamber 28a and serves as a heating element. A thermister 302 provides a feedback signal to the regulator 298 which in turn controls the drive to the transistor 300, thereby maintaining a substantially constant temperature within the ozonator 28 and thus further stabilizing the ozone concentration generated therein.

As will be recognized by those skilled in the art, the error detector 50 and the up-down counter 60 within the comparator 34 may be incorporated in a microcomputer. In an illustrative embodiment of an apparatus for producing adjustable concentrations of ozone within a carrier gas flow according to the present invention, the microcomputer determines the difference between the desired ozone concentration and the measured ozone concentration and accordingly adjusts a twelve bit binary number which is converted by the DAC 64 into the analog drive signal that is applied to lamp driver 29.

More particularly, when the microcomputer receives a strobe signal on the line 48 from the gas analyzer 20 (FIG. 1), the microcomputer converts the BCD signals appearing on the lines 46 and 54 representing concentrations in parts per million into respective binary numbers. The binary number representing desired ozone concentration is subtracted from the binary number representing measured ozone concentration and the result is divided by four. The remainder from this division is dropped and the result is then added to a twelve bit binary number that may be stored within memory and which is also applied through the lines 62 to the DAC 64. It will be appreciated that by dividing the result of the subtraction by four and by dropping a remainder which may result from the division, the microcomputer scales the difference between the measured and desired ozone concentration by a factor of four and also causes no change in the twelve bit binary number when the difference between the actual and measured ozone concentration is within a predetermined relatively narrow range.

It will be recalled from the description made with reference to FIGS. 1 and 3b that the analog output from the DAC 64 decreases as the binary input to the DAC 64 increases and vice versa. For example, if the desired ozone concentration is less than the measured concentration, then the result of the subtract will be a positive binary number. If this difference is at least equivalent to four, then this difference when divided by four will result in some positive binary number that is added to and thus increases the twelve bit binary number. The increased twelve bit binary number then causes the analog output of the DAC 64 to decrease, thus decreasing the ozone concentration produced by the ozonator 28.

Similarly, and by way of further example, if the measured ozone concentration is less than the desired concentration and if the difference is at least equivalent to four, then some negative binary number is added to and thus decreases the twelve bit binary number. This causes the analog output of the DAC 64 to increase to thereby increase the ozone concentration produced by the ozonator 28.

The microcomputer will continue to adjust the ozonator output until the difference between the desired and measured ozone concentrations is within the narrow range and will thereafter adjust the ozonator output to compensate for drift or other inaccuracies within the gas generator which may cause the difference to exceed the narrow range.

While an exemplary embodiment of the invention has been described, it is to be understood that the invention is not limited to the details herein explained. It is expected that given the teachings herein those skilled in the art will recognize numerous variations and equivalents which come within the spirit of the invention and which are intended to be included herein.

What is claimed is:

1. A method for generating a calibration gas flow including a concentration of a selected gas in a carrier gas comprising the steps of
   generating a first signal,
   providing a concentration of the selected gas within the carrier gas in response to the first signal,
   determining the concentration of the selected gas and generating a second signal proportional thereto,
   generating a third signal proportional to a predetermined concentration of the selected gas,
   comparing the second and third signals to determine the difference therebetween, and
   adjusting the first signal to decrease the difference between the second and third signals.

2. The method of claim wherein the predetermined concentration is adjustable.

3. The method of claim 1 wherein the step of adjusting the first signal includes the step of adjusting a plurality of digital signals.

4. The method of claim 3 wherein the step of generating the first signal includes the step of converting the plurality of digital signals into the first signal.

5. A method as in claim 1 wherein the concentration determining step occurs substantially periodically and the comparing step is performed in response to the completion of the concentration determining step.

6. A method for generating a calibration gas flow including a concentration of a selected gas in a carrier gas comprising the steps of
   generating a plurality of adjustable digital signals,
   converting the digital signals into an analog first signal,
   providing the selected gas within the carrier gas, the concentration of the selected gas being proportional to the first signal,
   determining the concentration of the selected gas and generating a second signal proportional thereto,
   generating a third signal proportional to an adjustable predetermined concentration of the selected gas,
   comparing the second and third signals to determine the difference therebetween, and
   adjusting the digital signals an amount proportional to the difference between the second and third signals in a direction required to decrease the difference between the second and third signals.

7. Method of claim 6 wherein the adjusting step further includes the steps of
   adjusting the digital signals a first amount proportional to the difference between the second and third signals when the difference is within a first range, and
   adjusting the digital signals a second amount proportional to the difference between the second and third signals when the difference is outside the first range.

8. A calibration apparatus for generating a concentration of a selected gas in a carrier gas comprising
   gas generator means for providing a selected gas in a carrier gas in response to a drive signal,
   analyzer means in communication with the gas generator means for determining the concentration of the selected gas in the carrier gas and for generating a first signal proportional thereto,
   concentration selector means for generating a second signal proportional to a concentration of the selected gas, and
   comparator means responsive to the first and second signals for adjustably generating the drive signal, for determining a difference between the first and second signals, and for adjusting the drive signal in a direction required to decrease the difference.

9. The apparatus of claim 8 wherein the comparator means includes
   first up-down counter means for generating a plurality of digital signals indicative of a count,
   means for receiving the digital signals and for converting the digital signals into the drive signal, and
   error detector means responsive to the first and second signals, the first counter means being responsive to the error detector means for adjusting the first counter means to decrease the difference.

10. The apparatus of claim 9 wherein the first and second signals respectively comprise a plurality of digital signals proportional to the detected concentration of the selected gas and to the selected concentration of the selected gas and the error detector means includes
    second up-down counter means presettable to the second signals for generating a third plurality of digital signals,
    means for providing a signal to the second counter means to enable said pesetting when the first signals are updated,
    digital comparator means responsive to the third signals and to the first signals for detecting a difference between the first and third signals and for applying pulses to the second up-down counter means until the third signals are equal to the first signals, and
    said first counter means being responsive to the error pulses to thereby adjust the count so as to decrease said difference.

11. A calibration apparatus for generating a predetermined concentration of a selected gas in a carrier gas comprising
    gas generator means responsive to a drive signal for providing an output of a selected gas in a carrier gas, the concentration of the selected gas being proportional to the drive signal,
    analyzer means in communication with the gas generator means output for determining the concentration of the selected gas in the carrier gas and for generating a first plurality of digital signals representing said concentration,
    concentration selector means for adjustably generating a second plurality of digital signals representing a desired concentration of the selected gas in the carrier gas,
    drive signal generator means for adjustably generating the drive signal, and
    error detector means responsive to the first and second plurality of signals for determining the difference therebetween and for providing an adjusting signal to the drive signal generator means to adjust the drive signal an amount proportional to the difference and in a direction required to decrease the difference.

12. The apparatus of claim 11 wherein the drive signal generator means includes a first up-down counter and the error detector means includes
    second up-down counter means having output signals presettable to the second signals,
    means for providing a signal to the second counter means to enable said presetting when the first signals are updated,
    digital comparator means responsive to the first signals and to the second counter means output signals for detecting a difference therebetween and for applying error pulses to the second counter means until the second counter output signals equal the first signals, and
    means for applying the error pulses to the first counter means to thereby adjust the first counter means to decrease the difference.

13. The apparatus of claim 12 wherein the pulse applying means includes
    third counter means responsive to the error pulses for dividing the error pulses by a predetermined number and for generating an output signal, and
    selector means for applying the third counter means output signal to the first up-down counter means for a predetermined number of error pulses and for otherwise connecting the error pulses to the first up-down counter means.

14. A calibration apparatus for generating an output of a predetermined concentration of a selected gas in a carrier gas, comprising
    gas generator means responsive to a drive signal, for providing an output of a gas, the concentration of the selected gas being substantially proportional to the drive signal,
    analyzer means in communication with the gas generator means output for determining the concentration of the selected gas in the carrier gas and for generating a first signal proportional thereto,
    concentration selector means for generating a second signal proportional to a concentration of the selected gas,
    microcomputer means for generating a plurality of digital signals proportional to an adjustable drive number, and
    means for converting the digital signals into the drive signal, the microcomputer means being further responsive to the first and second signals for determining the difference therebetween and for adjusting the drive number to decrease the difference.

15. The apparatus of claim 14 wherein the microcomputer means performs said adjustment when the difference is greater than a predetermined amount.

* * * * *